(12) United States Patent
Doerr et al.

(10) Patent No.: US 8,942,825 B2
(45) Date of Patent: Jan. 27, 2015

(54) IMPLANTABLE DEVICE WITH ELONGATED ELECTRICAL CONDUCTOR

(75) Inventors: Thomas Doerr, Berlin (DE); Ingo Weiss, Berlin (DE)

(73) Assignee: Biotronik SE & Co. KG, Berlin (DE)

(*) Notice: Subject to any disclaimer, the term of this patent is extended or adjusted under 35 U.S.C. 154(b) by 660 days.

(21) Appl. No.: 13/301,651

(22) Filed: Nov. 21, 2011

(65) Prior Publication Data

US 2012/0157810 A1 Jun. 21, 2012

Related U.S. Application Data

(60) Provisional application No. 61/424,073, filed on Dec. 17, 2010.

(51) Int. Cl.
*A61N 1/37* (2006.01)
*A61N 1/05* (2006.01)
*A61B 18/14* (2006.01)
*A61N 1/08* (2006.01)

(52) U.S. Cl.
CPC .............. *A61N 1/05* (2013.01); *A61B 18/1492* (2013.01); *A61N 1/056* (2013.01); *A61N 1/08* (2013.01); *A61N 2001/086* (2013.01)
USPC .......................................... 607/119; 607/122

(58) Field of Classification Search
CPC ... A61N 1/056; A61N 1/08; A61N 2001/086; A61B 18/1492
USPC .................................. 600/374; 607/119, 122
See application file for complete search history.

(56) References Cited

U.S. PATENT DOCUMENTS

| | | | |
|---|---|---|---|
| 2006/0247684 A1 | 11/2006 | Halperin et al. | |
| 2006/0252314 A1 | 11/2006 | Atalar | |
| 2008/0132985 A1 | 6/2008 | Wedan et al. | |
| 2008/0243218 A1* | 10/2008 | Bottomley et al. | ............ 607/116 |
| 2009/0149920 A1 | 6/2009 | Li | |
| 2010/0217262 A1 | 8/2010 | Stevenson et al. | |
| 2011/0196460 A1 | 8/2011 | Weiss | |

FOREIGN PATENT DOCUMENTS

WO  2008/115426 A1  9/2008

OTHER PUBLICATIONS

European Search Report dated Dec. 18, 2012, 9 pages.

\* cited by examiner

*Primary Examiner* — Tammie K Heller
(74) *Attorney, Agent, or Firm* — ARC IP Law, PC; Joseph J. Mayo (57) ABSTRACT

A temporarily or permanently implantable medical device having at least one elongated electrical function conductor for transmitting therapeutic signals or diagnostic signals or both. At least one additional conductor is provided which together with the function conductor forms, at least in places, a double line which is separated from the function conductor by a dielectric and which is coupled to the function conductor via a coupling impedance. The coupling impedance is dimensioned so that the value of the line wave impedance of the function conductor for frequency ranges far above a frequency range of the therapeutic or diagnostic signals is much greater than the in the frequency range of the therapeutic or diagnostic signals, so that currents in a frequency range above the frequency range of the therapeutic or diagnostic signals are damped more intensely than the currents which form therapeutic or diagnostic signals.

14 Claims, 10 Drawing Sheets

IMPLANTABLE DEVICE WITH ELONGATED ELECTRICAL CONDUCTOR

This application claims the benefit of U.S. Provisional Patent Application 61/424,073 filed on 17 Dec. 2010, the specification of which is hereby incorporated herein by reference.

BACKGROUND OF THE INVENTION

1. Field of the Invention

Embodiments of the invention relate to a permanently or temporarily implantable device having an elongated electrical conductor.

2. Description of the Related Art

Such devices, for example electrode lines for electrostimulation or catheters, have the disadvantage that their electrical conductor may heat up during magnetic resonance imaging due to the fact that the alternating magnetic fields which are present induce considerable electrical currents in the electrical conductor. In addition, such induced currents may be delivered to surrounding tissue via electrode poles of the electrode line, resulting in undesired heating of the tissue, for example. For this reason, there is presently little or no possibility for cardiac pacemaker patients to be tested using magnetic resonance imaging.

Implantable cardiac pacemakers or defibrillators (also jointly referred to below as cardiac stimulators or implantable pulse generators (IPG)) are typically connected to at least one stimulation electrode line, which at its proximal end which is provided for connection to the cardiac pacemaker or defibrillator has a standardized electrical terminal, and at its distal end which is provided for placement in the heart has one or more electrode poles. Such an electrode pole is used to deliver electrical pulses to the (myocardial) tissue of the heart or for sensing electrical fields in order to sense an activity of a heart. For these purposes, electrode poles typically form electrically conductive surface sections of an electrode line. Electrode poles are typically provided as an annular electrode in the form of a ring around the electrode line, or in the form of a point electrode or tip electrode at the distal end of the electrode line. At their proximal end the electrode poles are connected in an electrically conductive manner via one or more electrical conductors to contacts of the electrical terminal of the electrode line. Thus, the electrode lines at their proximal end extend between the contacts of the electrical terminal, and at the distal end one or more electrical conductors which electrically connect the one or more electrode poles to the one or more contacts extend between the electrode poles. These electrical conductors may be used on the one hand for transmitting stimulation pulses to the electrode poles, and on the other hand for transmitting electrical signals received via the electrode poles to the proximal end of the electrode line, and in the description below are also referred to in each case as a function line. Such function lines are electrical conductors which are necessary for the functions of the particular electrode line, and are thus subject to the risk of electrical currents being induced therein as the result of external alternating magnetic fields which, for example, may lead to undesired heating of the function lines or the electrode poles connected thereto, or may result in the discharge of corresponding currents via the electrode poles to surrounding tissue, and thus heating of the surrounding tissue.

BRIEF SUMMARY OF THE INVENTION

The object of one or more embodiments of the invention is to provide a device that eliminates the above-described problem.

According to one or more embodiments of the invention, this object is achieved by a permanently or temporarily implantable medical device having at least one elongated electrical function conductor for transmitting therapeutic signals or diagnostic signals or both, wherein at least one additional conductor is provided which together with the function conductor forms, at least in places, a double line which is separated from the function conductor by a dielectric and which is coupled to the function conductor via a coupling impedance. The coupling impedance is dimensioned in such a way that the value of the line wave impedance of the function conductor for frequency ranges far above a frequency range of the therapeutic or diagnostic signals is much greater than the value of the line wave impedance of the function conductor in the frequency range of the therapeutic or diagnostic signals, so that currents in a frequency range above the frequency range of the therapeutic or diagnostic signals are damped more intensely than the currents which form therapeutic or diagnostic signals.

It is noted at this point that the terms "function conductor" and "therapy-providing conductor" are used synonymously.

The wave impedance is a measure of the wavelength-dependent value of the electrical resistance of HF cables.

In coaxial cables, the wave impedance is independent of the cable length, but is dependent on the capacitance and inductance per unit length of the HF cable. These values are a direct function of the diameter of the internal conductor and the shielding, and of the dielectric constants of the dielectric. The capacitance and inductance per unit length of a HF cable may be represented in the equivalent circuit diagram by a series connection of numerous individual inductors and a parallel connection of the same number of capacitors. Disregarding the ohmic resistance, the wave impedance (Z) results approximately from the square root of the ratio of the inductance to the capacitance.

One or more embodiments of the invention encompasses the concept of adjusting the wave impedance of a function conductor in such a way that the function conductor has a high wave impedance for frequency ranges which correspond to those for expected interference fields, and correspondingly damps currents at this frequency.

In a continuation of the inventive concept, this is achieved using an appropriately designed sheath wave trap, preferably in that the section of the medical device forming a double line is provided as a sheath wave trap.

The medical device is preferably an electrode line for connection to a cardiac stimulator.

Alternatively, the medical device is a catheter for electrophysiological interventions, or an electrode line for a temporary cardiac stimulator.

The coupling impedance between the function conductor and the additional conductor is preferably provided by a capacitor. Alternatively or additionally, the coupling impedance may be provided by an inductor and/or a short circuit.

According to alternative advantageous embodiments, the section of the medical device provided as a double line may be designed as a coaxial line, parallel line, strip line, or the like.

One embodiment of the invention is particularly preferred in which the section of the medical device provided as a double line is structurally integrated into the medical device in such a way that the geometric distance between the function conductor and the additional conductor which is spanned by the coupling impedance (a capacitor, for example) is short in comparison to the wavelength in the double line for a specified maximum working frequency. The ratio of the geometric distance between the function conductor and the additional conductor to the wavelength at a specified maximum working frequency is preferably less than one-tenth ($\frac{1}{10}$).

One design variant is particularly preferred in which the medical device is a single- or multipole, temporarily usable catheter or a permanently implantable electrode line or an elongated electrically conductive implant having partial insulation, so that localized heating is expected at defined electrode surfaces as the result of MRI-induced currents. At the proximal end of an electrode pole a second conductor (referred to here as "additional conductor") is provided, at least in places, around or near the supply line wire (therapy-providing conductor, referred to here as "function conductor"), and together with the therapy-providing conductor forms a double line on this section, the conductors being insulated from one another by a dielectric. The ends of the second conductor, i.e., of the additional conductor, are connected to one another by an impedance whose value is specified as a function of the inductance and capacitance per unit length of the double line section in such a way that the therapeutic supply line has a high impedance (i.e., in the present case, intensely damps currents) for frequencies significantly higher than those of therapeutic and diagnostic signals, and in particular for at least an HF frequency typical of MRI, with the objective of reducing/preventing the undesired implant/electrode heating during magnetic resonance imaging/spectroscopy.

The double line section is preferably implemented in such a way that the one conductor is the therapy-providing function conductor itself, which for realizing the sheath wave trap is uninterrupted, in that the sheath wave trap is situated around or immediately adjacent to the function conductor. In that case, potentially unreliable contacting techniques on the therapy-providing conductor (function conductor) itself are not necessary.

The double line section is preferably coiled, i.e., provided with a helical design.

One design variant is particularly preferred in which the double line section forms a loop which is guided parallel to the function conductor or the function conductors, i.e., the therapy-providing conductors, in the electrode supply line, or for coiled electrode line designs, is wound into the coil gaps.

For cable electrodes, in which the therapy-providing function conductor is a cable conductor, the function conductor is preferably designed as a coiled structure in the double line section (coaxial section), so that the function conductor is helically coiled in the section of the medical device provided as a double line.

The insulation of the therapy-providing conductor, i.e., the function conductor, itself is preferably used as dielectric. The second conductor of the double line, i.e., the additional conductor, may then be implemented by metal plating of the dielectric (for example by vapor deposition of a metal layer), and may thus be formed, for example, by a vapor-deposited metal layer. This results in a likewise simple and compact design of the double line section.

Alternatively, the additional conductor, for example the coaxial external conductor, may be made of a flexible conductive polymer or liquid crystal polymer (LCP).

The double line section may also be incorporated into the electrode line as a separately manufactured component, using conventional connection technology.

The double line section preferably has a wave impedance of less than 120 ohms.

Figure 5:
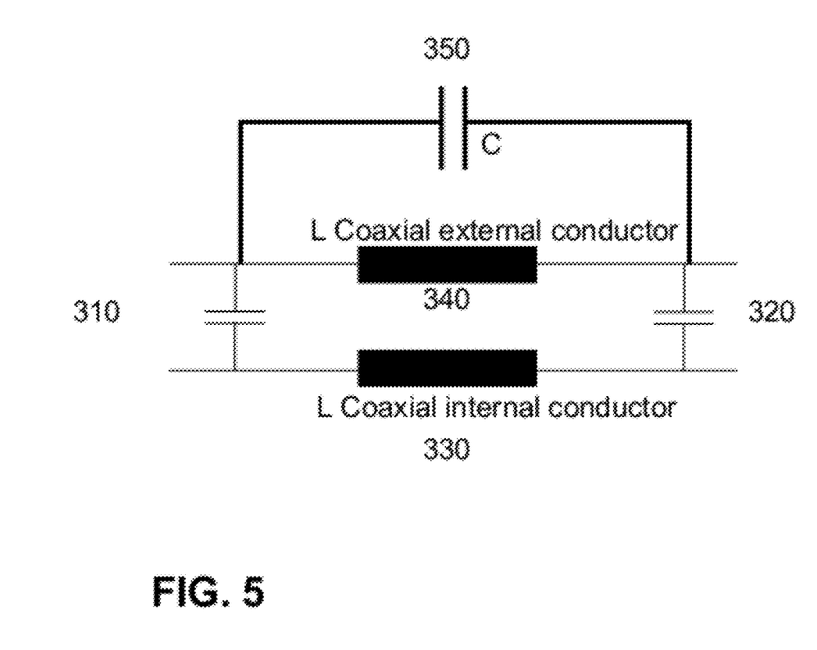
FIG. 5 shows a simplified equivalent circuit diagram of the implementation of a sheath wave trap according to an embodiment of the invention.
Figure 6:
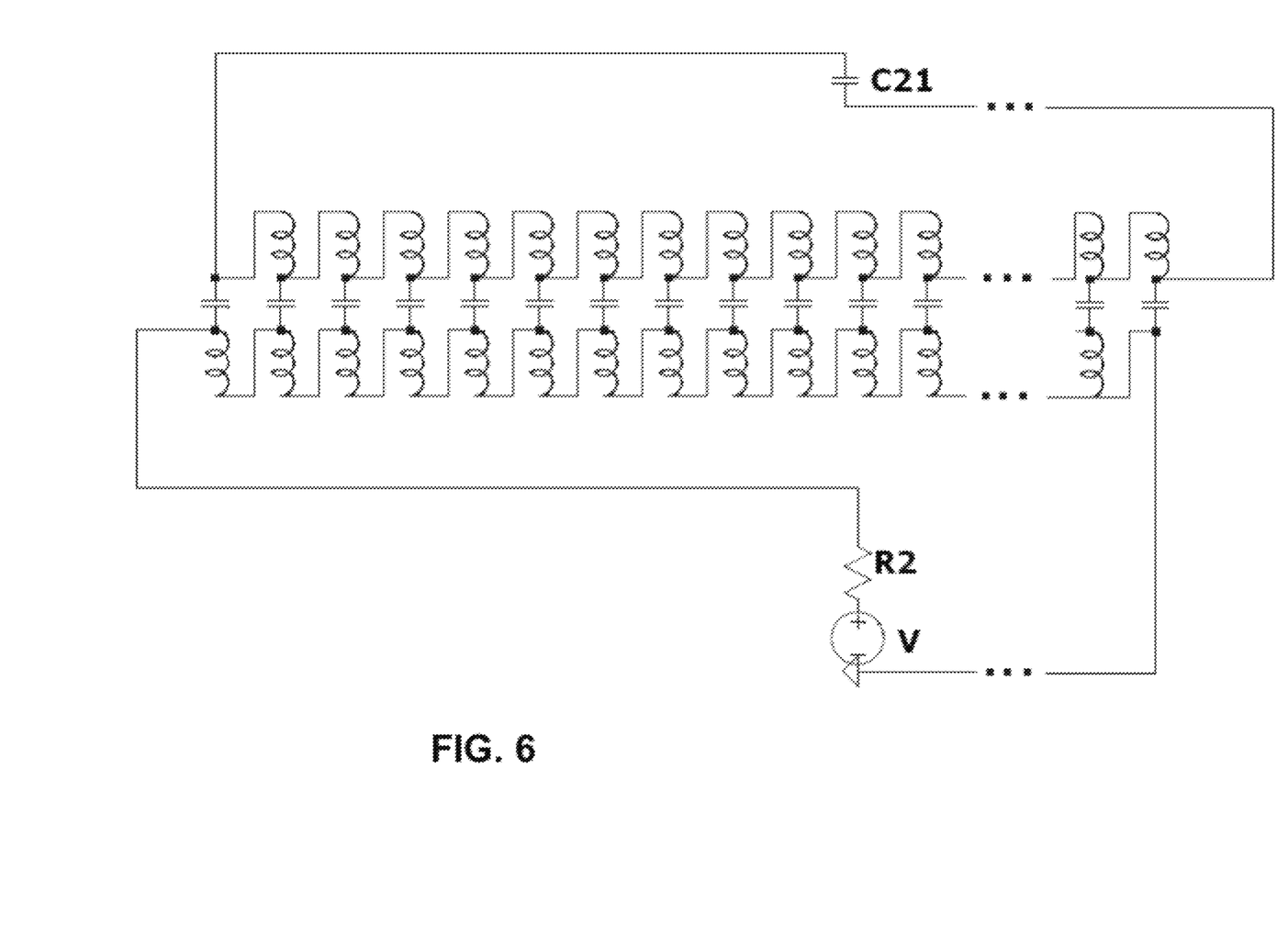
FIG. 6 shows a more detailed equivalent circuit diagram (SPICE model) which represents the double line discretized as an LC network.

The double line section may also be implemented by a discrete component, in particular preferably having fewer than 20 subsections (i.e., "La-Cc-Lb cells"), as shown in the equivalent circuit diagrams in FIGS. 5 and 6.

The double line section may also be designed as a hybrid, as a line but with a dielectric interrupted one or more times along the line, thus discretely implementing the capacitors Cc.

The double line section is preferably designed in such a way that the losses (series resistances of the conductors, i.e., of inductors La and Lb or parallel resistances of capacitors Cc;) are coordinated in such a way that the bandwidth around the resonance frequency (frequencies) is less than 10 MHz.

The sheath wave trap according to one or more embodiments of the invention is preferably designed in such a way that the damping of the (heat-producing) current caused by the sheath wave trap for the particular Larmor frequency of magnetic resonance imaging or spectroscopy is greater than 6 dB.

The ratio of the inductance per unit length of the individual conductors of the double line (corresponding to the ratio La/Lb in FIG. 6) is between 0.1 and 10, and Lb/La is preferably 0.75.

The double line section is preferably designed in such a way that, using the parameters of the sheath wave trap formed by the double line section, the frequency spacings of the resonances are optimized so that the maximum possible number of HF working frequencies of MRI devices are achieved using the same sheath wave trap (and therefore the same electrode line). The resonances are preferably as close as possible to one another, having a frequency spacing of less than 25 MHz.

In addition to the embodiments described herein other alternative embodiments may include some or all of the disclosed features.

BRIEF DESCRIPTION OF THE DRAWINGS

Embodiments of the invention are explained in greater detail with reference to the figures, which show the following.

DETAILED DESCRIPTION OF THE INVENTION

Figure 1:
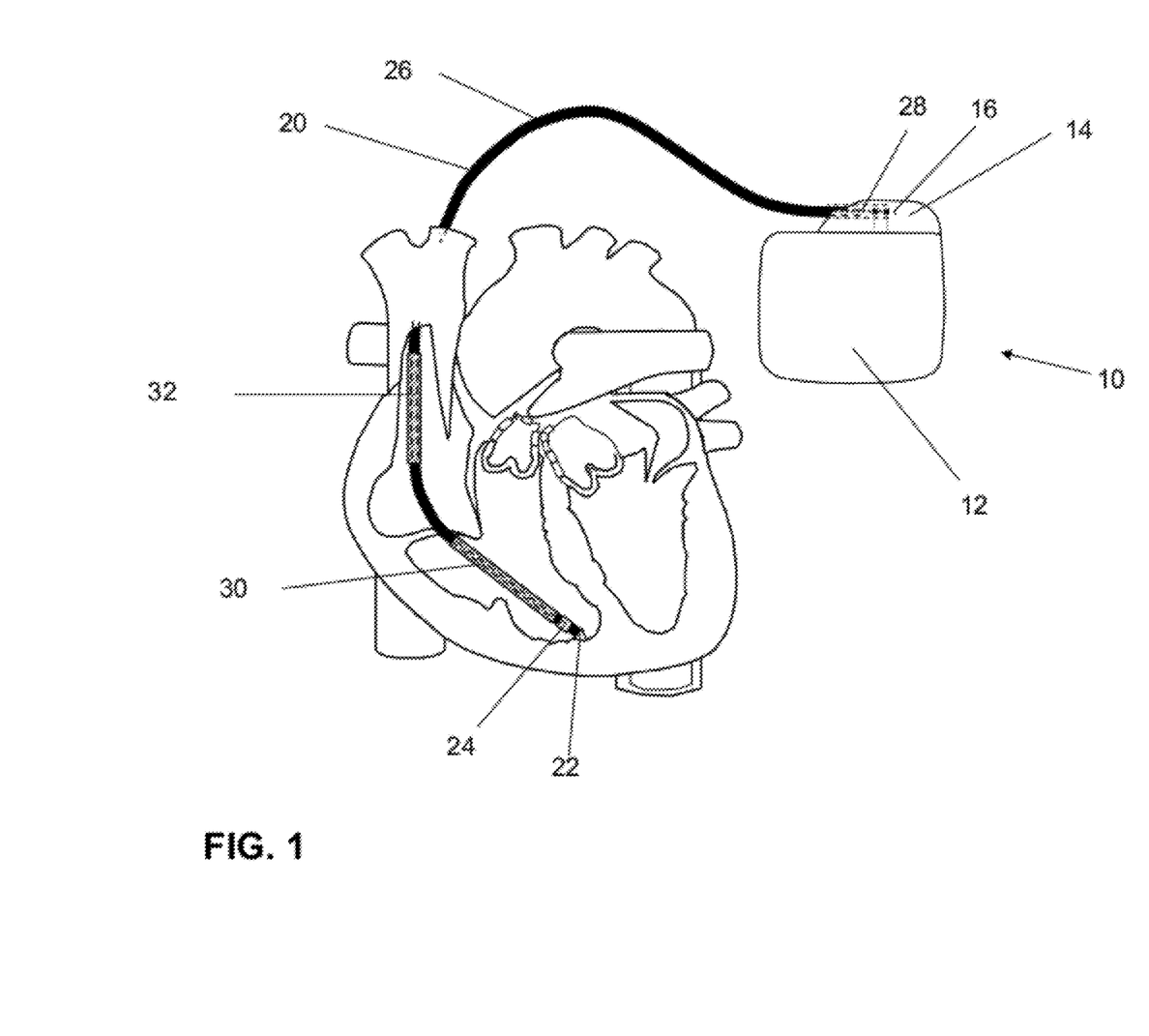
FIG. 1 shows as an implantable medical device an implantable cardiac stimulator 10 and an implantable electrode line 20 connected thereto.

The implantable cardiac stimulator 10 may be a cardiac pacemaker or a cardioverter/defibrillator (ICD). In the illustrated exemplary embodiment, the cardiac stimulator 10 is a ventricular cardiac pacemaker and defibrillator. Other known cardiac stimulators are dual-chamber cardiac pacemakers for stimulating the right atrium and the right ventricle, or biventricular cardiac pacemakers, which in addition to the right ventricle are also able to stimulate the left ventricle.

Such stimulators typically have a housing 12, which is generally made of metal and is therefore electrically conductive, and which may be used as a large-surface electrode pole. A connector housing 14, also referred to as a header, is typically affixed to the exterior of the housing 12. Such a header typically has contact sockets for accommodating plug contacts. The contact sockets have electrical contacts 16 which are connected via appropriate conductors to an electronics system situated in the housing 12 of the cardiac stimulator 10.

The electrode line 20 likewise represents an implantable medical device within the meaning of one or more embodiments of the invention. Electrode poles in the form of a point electrode or tip electrode 22 and an annular electrode 24 present in the vicinity thereof are situated in a manner known per se at the distal end of the electrode line 20. The electrode poles 22 and 24 are designed in such a way that, depending on the function of a cardiac stimulator to which the electrode line 20 is connected, they are provided to sense electrical potentials of the cardiac tissue (myocardium) or to supply electrical signals, for example for delivering stimulation pulses to the cardiac tissue which surrounds them. FIG. 1 shows the manner in which the electrode poles, i.e., the tip electrode 22 and the annular electrode 24, and for the present application, the electrode line 20, are located in the apex of a right ventricle of a heart.

The tip electrode 22 and the annular electrode 24 are in each case electrically connected via at least one electrical conductor 26 to a plug contact 28 at the proximal end of the electrode line 20. The plug contact 28 has electrical contacts which correspond to the electrical contacts 16 of the contact socket in the connector housing 14 of the implantable cardiac stimulator. The electrical conductors 26 in the electrode line 20 may be designed as somewhat elongated cable conductors or as helically coiled conductors. Such conductors, which connect functional electrode poles to electrical contacts of the plug contact at the proximal end of the electrode line 20 in an electrically conductive manner, are referred to as function conductors within the scope of this description, since, for example, they transmit electrical signals used for the treatment from the plug contact to the particular electrode pole, or conduct sensed signals which represent electrical potentials from the particular electrode pole to the plug contact, and are thus used for the fundamental function of the medical device.

The electrical conductors 26 which connect the electrode poles 22 and 24 to the electrical contacts of the plug 28 of the electrode line 20 are enclosed over most of their length by an insulating sheath, resulting in targeted electrical contact with the tissue of the heart via the electrode poles.

In addition to the electrode poles 22 and 24, which are typically used for stimulation (in this case, ventricular) of the cardiac tissue, the electrode line 20 has two large-surface electrode poles 30 and 32, which are used as defibrillation electrodes and are formed by at least one bare helically wound wire.

It is pointed out that within the scope of this exemplary embodiment the invention is explained with reference to a right ventricular cardiac pacemaker and defibrillator. As a medical device within the meaning of one or more embodiments of the invention, however, in principle an ablation electrode line may also be used, which in the application likewise extends into the heart of a patient and is controlled by a device located outside the patient, and for this purpose is connected to the device.

Figure 2:
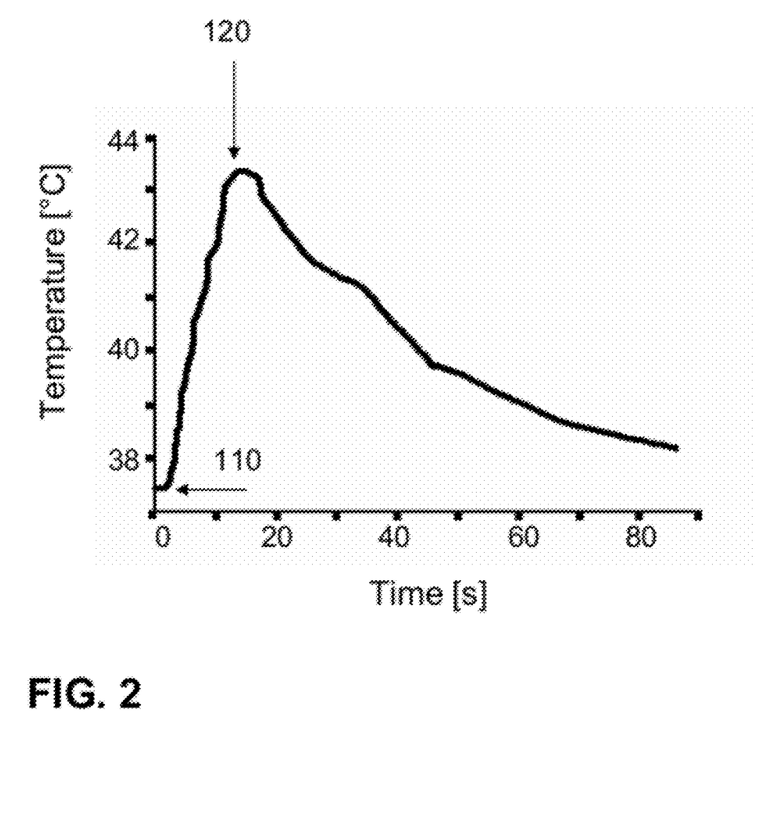
FIG. 2 shows an example of a temperature curve at the electrode tip under the influence of high-frequency alternating fields, such as those occurring in magnetic resonance imaging (MRI).

FIG. 2 illustrates a typical temperature curve 100 of a conventional pacemaker/ICD electrode in magnetic resonance imaging (MRI). The temperature increases rapidly when the high-frequency alternating field in the MRI unit is switched on at time 110, the steepness of the increase and the maximum achievable temperature being greatly dependent on the electrode position relative to the high-frequency alternating fields of the MRI. When the high-frequency alternating field is switched off at time 120, the electrode tip quickly cools due to its relatively low heat capacity.

Figure 3:
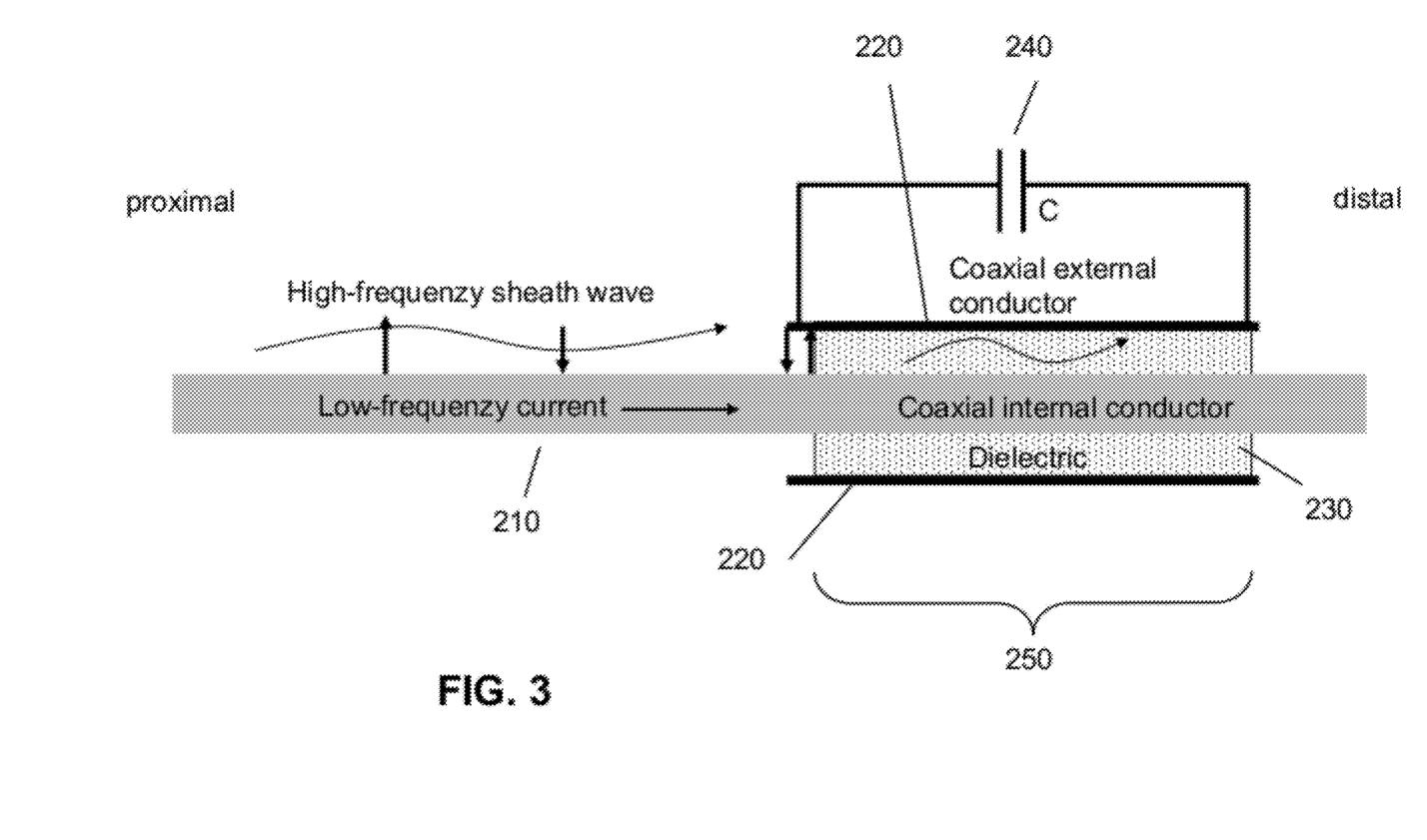
FIG. 3 shows the design of a ferrite-free sheath wave trap.

FIG. 3 illustrates the design of the ferrite-free sheath wave trap. In FIG. 3 the conductor 210 is shown in elongated form for simplicity, although in general the conductors may also be coiled. The line section in the region of reference numeral 250 forms a double line section in which a dielectric 230 separates the conductor 210, namely, the function conductor, and the additional conductor 220 from one another. Line section 250, also referred to as "double line" below, may be implemented as a coaxial conductor, parallel conductor, strip line, or the like; the designs are described below on the basis of coaxial conductors without exclusion of universality. In the exemplary embodiment illustrated, the function conductor 210 forms a coaxial internal conductor within the double line section 250, and the additional conductor is the coaxial external conductor 220.

According to one preferred implementation, this conductor section is coiled. According to the implementation, the geometric distance spanned by the capacitor 240 is short in comparison to the wavelength in the double line for the highest working frequency (preferably a factor of $<1/10$). According to one feature of an embodiment of the invention, a coil may be realized, also in the case of cable electrodes, so as to achieve this short distance. Another preferred variant is shown in FIG. 4.

Capacitor C 240 feeds the field exiting at the distal end of the coaxial external conductor 220 on a short electrical path in a phase-reversed manner back to the proximal input in the coaxial section 220, thus suppressing the sheath wave. The high-frequency signals are conducted due to the skin effect at the surface; i.e., the fields are propagated even by the surrounding insulation (displacement currents). These are therefore referred to as sheath waves. On the other hand, the low-frequency therapeutic currents flow inside the conductor. The trap according to an embodiment of the invention is designed to block only the sheath waves, which thus transport the undesired HF energy.

Figure 4:
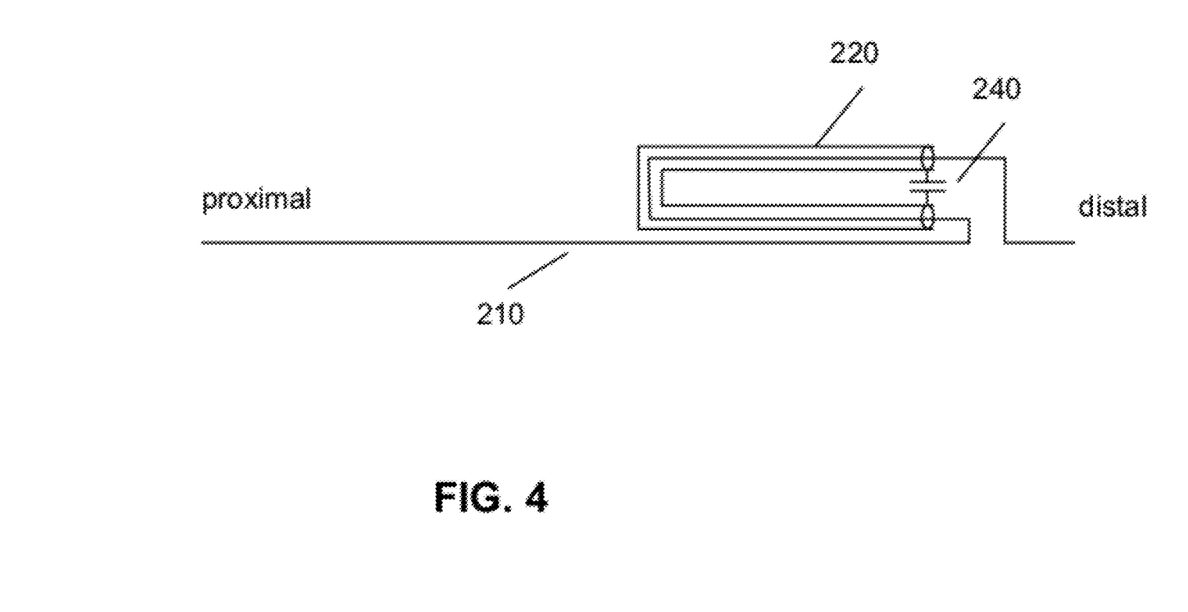
FIG. 4 shows a preferred incorporation of a sheath wave trap into an electrode line.

FIG. 4 shows a preferred incorporation of a sheath wave trap into an electrode line. The sheath wave trap implemented from 220 and 240 (with the dielectric (not shown) in-between) is preferably installed close to the distal end of the electrode line, preferably in the distal-side half of the electrode line.

One or more embodiments of the invention include one conductor of the double line that is implemented by the therapeutic conductor (the function conductor) of the electrode supply line itself, while the dielectric and second conductor (additional conductor) are guided only next to or around same, i.e., without having to mechanically interrupt the therapeutic conductor. This is a beneficial reliability feature of the approach according to this embodiment of the invention. The capacitor connects the ends of the additional conductor. In the present case the contacting is relevant only for the MRI properties of the electrode, but not for the lifelong therapeutic reliability of the electrode.

A sheath wave trap is implemented in the described manner by interconnecting the double line having such a design with the capacitor 240. According to one or more embodiments of the invention, this is achieved in such a way that the sheath wave trap is resonant at least one frequency. The effect is at a maximum at this resonance frequency or at the multiple resonance frequencies. According to one or more embodiments of the invention, these resonance frequencies are applied in such a way that they are close to the working frequency of common MRI devices (see Table 1), in particular in such a way that the bandwidths of these resonances are 10 MHz maximum.

According to the prior art, ferrites are used as sheath wave traps for the frequency range of conventional MRI devices. However, these become saturated in the static field of the MRI and therefore become ineffective. Thus, an object of one or more embodiments of the invention is to develop an approach without ferrites.

Figure 8A:
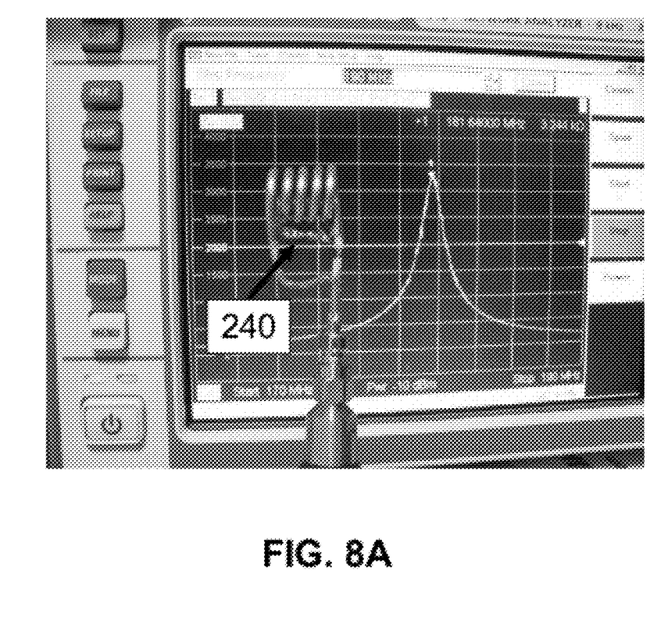
FIGS. 8A and 8B show an implementation form of a sheath wave trap designed as a coil, using coaxial technology.
Figure 8B:
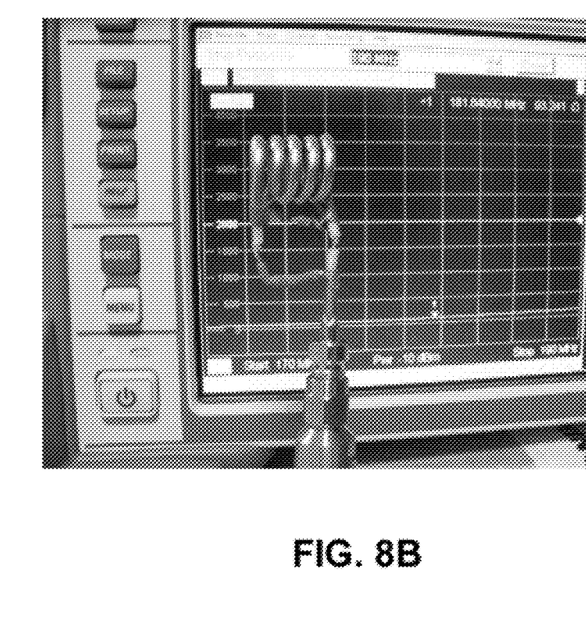

One described implementation is the coiled design. A few windings are generally sufficient, since the capacitor C 240 as well does not require long supply lines, which otherwise would have an undesired parasitic inductance. One design variant is illustrated in FIGS. 8A-B by way of example.

FIG. 5 illustrates the equivalent circuit diagram of the ferrite-free sheath wave trap according to an embodiment of the invention, which in the exemplary embodiment in FIG. 3 is designed as a coaxial line section. In the equivalent circuit diagram the internal conductor is represented by the inductor 330, the external conductor is represented by the inductor 340, and the dielectric is represented by the coupling capacitors 310, 320. The additional capacitor 350 causes a phase shift, thus destructively feeding back the sheath wave. It is important to note that, although the coaxial internal conductor in the equivalent circuit diagram is illustrated as an inductor 330, in its design it is not interrupted by an additional component, or the illustrated coupling capacitors 320 are connected to this therapy-providing function conductor.

FIG. 6 shows a more detailed equivalent circuit diagram in the form of a SPICE model which represents the double line discretized as an LC network. It is also taken into account that the elements are actually loss-impaired (not illustrated, but taken into consideration in the SPICE model). The capacitor denoted by reference numeral 240 or 350 in the previous figures is denoted in the present case by C21. The resistor and the voltage source are included in the measuring circuit which illustrates the mode of operation. For an actual electrode, the current which flows through the measuring shunt R2 would flow into the tissue and accordingly heat same during magnetic resonance imaging.

Figure 7A:
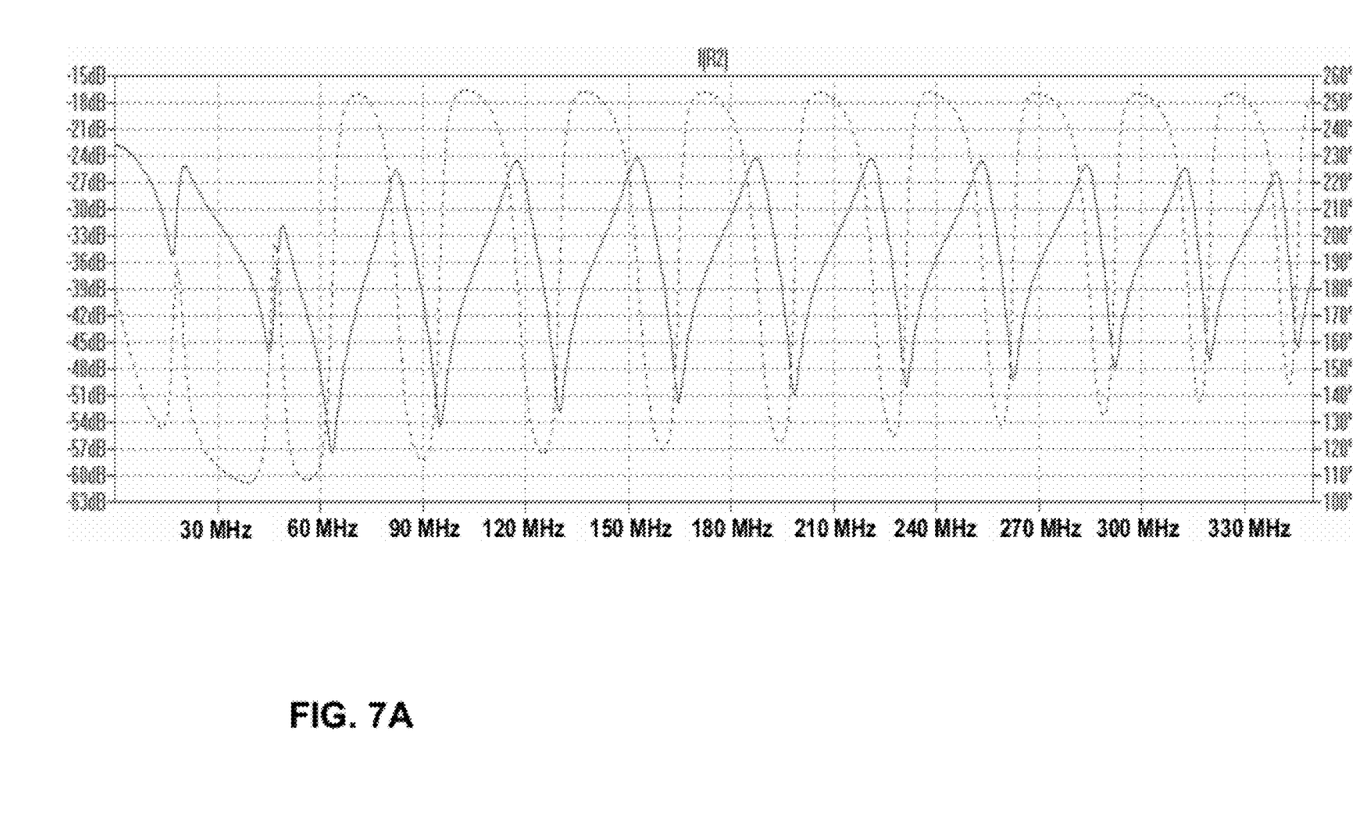
FIGS. 7A and 7B show the characteristics of two electrode lines having different designs of the sheath wave trap.

FIG. 7A shows the result of a simulation based on the SPICE model from FIG. 6 for a multiresonant sheath wave trap according to the inventive principle, which is optimized for effectively protecting the same electrode for all three MRI devices listed in Table 1. The effect is particularly pronounced at the frequencies for which the current is intensely damped. The amplitudes and phase position of the current in the measuring shunt are shown.

Figure 7B:
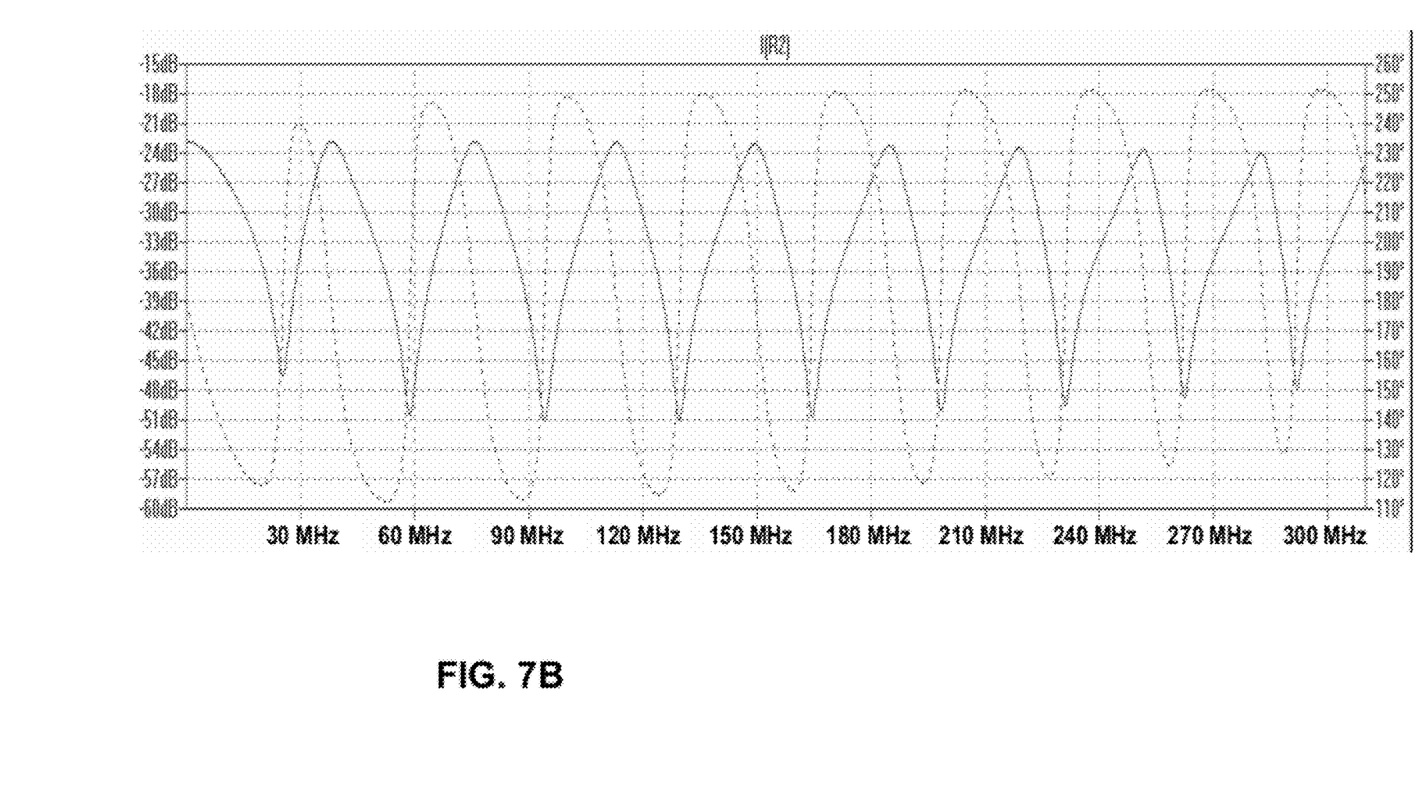

FIG. 7B shows the result of a similar simulation in which the modeled sheath wave trap uses an inductor instead of capacitor 240 or C21. In this case only the similar effect from a phenomenological standpoint is shown. The desired frequencies may thus be achieved by appropriate parameter adjustments.

TABLE 1

| Frequency (MHz)/MRI magnetic field strength (T) | Damping (dB) of the current relative to a signal at 1 kHz | Reduction in heating by (%) |
| --- | --- | --- |
| 63.5 MHz/1.5 T | 34.5 dB | 99.9% |
| 126.9 MHz/3 T | 20.3 dB | 99.0% |
| 296.1 MHz/7 T | 17 dB | 98.0% |

Table 1 shows working frequencies in a gyromagnetic ratio of 42.3 MHz/T for protons. The effect of the design variant upon which FIG. 7A is based is stated in relation to a therapeutic/diagnostic useful signal at 1 KHz, since up to this frequency the electrode must function undamped to the greatest extent possible for therapeutic and diagnostic reasons.

For physical reasons, the resonances of the sheath wave trap according to one or more embodiments of the invention are located in specific frequency spacing ratios. Therefore, the desired working frequencies of MRI devices are not all achieved equally well. However, the optimization of the components illustrated in FIG. 4 (in particular also with regard to the losses, desired in this case, for broadening the resonance depth) allows a fairly good compromise.

One preferred implementation in this regard is as follows, in which the line is discretized into 40 segments. The actual line to be used must be designed in such a way that it has the same behavior as the equivalent circuit diagram having the following values:
Conductor inductances $$La=7.4e\text{-}9(H);$$

$$Lb=0.75*La(H);$$

having the following serial loss resistances:

$$RLa=0.1\text{ (ohm)};$$

$$RLb=0.1\text{ (ohm)};$$

The line should have a wave impedance of $$Z0=18.75\text{ (ohm)};$$

from which the case capacitance per segment is calculated to be $$Cc=(La+Lb)/Z0^2(F);$$

having a parallel loss resistance of $$CcRp=1\text{ }e6\text{ (ohm)};$$

The source resistance (which at the same time is the measuring shunt) assumed here is $$Rq=20\text{ ohm}.$$

One implementation form designed as a coil is shown in FIGS. 8A-B. The illustrated implementation is by way of example only; therefore, the resonance in this case is not for a typical MRI frequency, but may be easily tuned thereto using an appropriate capacitor. The embodiment illustrated in FIG. 8 shows a coiled implementation of the sheath wave trap, using coaxial technology. The impedance is plotted on the screen shown in the background; a distinct peak is discernible when the capacitor 240 joins the coaxial external conductor at its ends (FIG. 8A). This is not the case when the capacitor is absent (FIG. 8B).

Figure 9A:
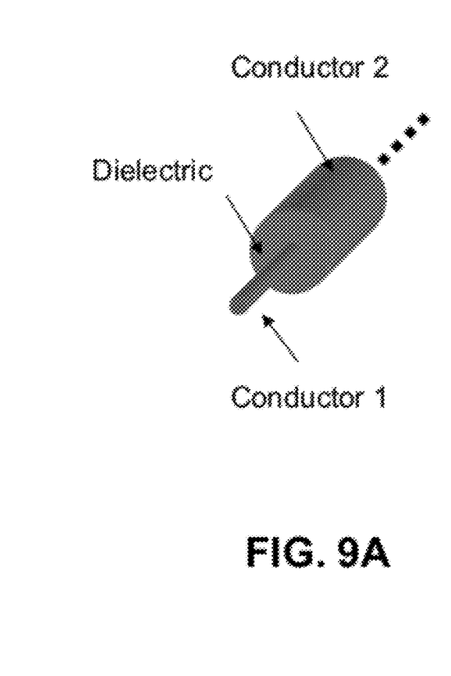
FIGS. 9A through 9C show various exemplary embodiments of a double line.
Figure 9B:
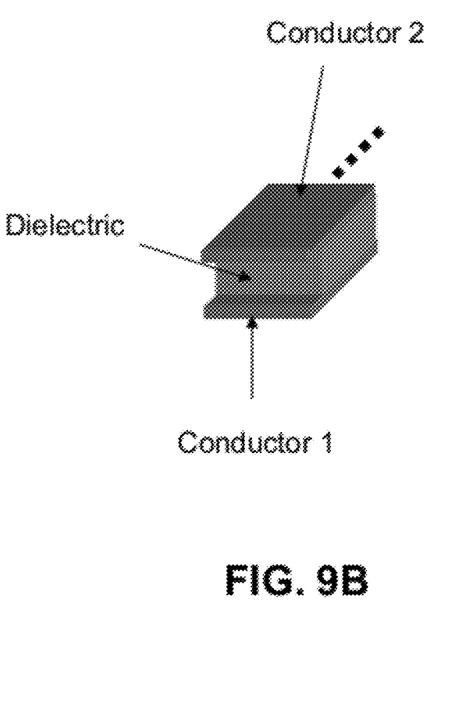
Figure 9C:
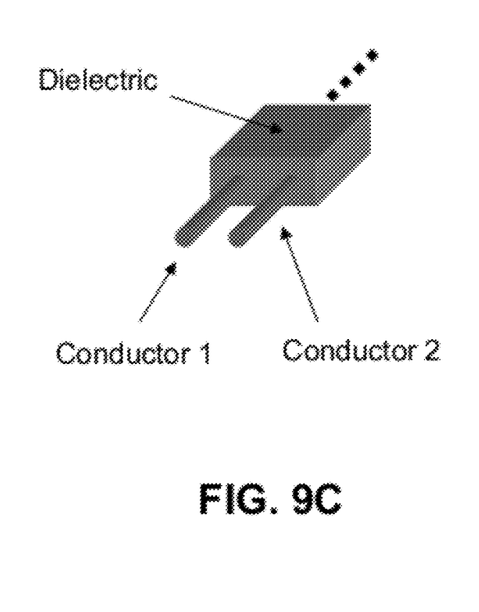

FIGS. 9A through 9C show various exemplary embodiments of a double line. In FIG. 9A the double line section is designed as a coaxial conductor. In FIG. 9B the double line section is designed as a parallel line of two flat conductors. In FIG. 9C the double line section is designed as a parallel line of two strip conductors.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of embodiments of this invention.

What is claimed is:

1. An implantable medical device comprising:
a function conductor comprising at least one elongated electrical function conductor configured to transmit therapeutic signals or diagnostic signals or both;
a dielectric; and,
an additional conductor comprising at least one additional conductor which together with the function conductor forms, in one or more places, a double line which is separated from the function conductor by the dielectric and which is coupled to the function conductor via a coupling impedance, which is dimensioned in such a way that the value of a line wave impedance of the function conductor for a frequency range above a frequency range of the therapeutic or diagnostic signals is much greater than the line wave impedance of the function conductor in the frequency range of the therapeutic or diagnostic signals, so that currents in the frequency range above the frequency range of the therapeutic or diagnostic signals are damped more intensely than the currents which form therapeutic or diagnostic signals,
wherein the one or more places of the medical device forming the double line is configured as a sheath wave trap.

2. The implantable medical device according to claim 1, wherein the medical device is an electrode line configured to connect to an implantable cardiac stimulator.

3. The implantable medical device according to claim 1, wherein the coupling impedance is provided by a capacitor.

4. The implantable medical device according to claim 1, wherein the coupling impedance is provided by an inductor.

5. The implantable medical device according to claim 1, wherein the one or more places of the medical device provided as the double line comprises a coaxial line, or parallel line, or strip line.

6. The implantable medical device according to claim 1, wherein the one or more places of the medical device provided as the double line is structurally integrated into the medical device in such a way that a geometric distance between the function conductor and the additional conductor which is spanned by the coupling impedance is short in comparison to a wavelength in the double line for a specified maximum working frequency.

7. The implantable medical device according to claim 1, wherein the additional conductor is situated at a proximal end of an electrode pole and is near a supply line wire, at least in places, or surrounds said supply line wire, at least in places, and thus together with the function conductor forms the double line at least in said places, wherein the function and additional conductors are insulated from one another by the dielectric, and an end of the function conductor is connected to an impedance whose value is provided as a function of the inductance and capacitance per unit length of the double line in such a way that the function conductor has a high impedance for frequencies significantly higher than those of therapeutic and diagnostic signals.

8. The implantable medical device according to claim 1, wherein the function conductor is not interrupted and has a one-piece design, and the sheath wave trap is situated around or immediately adjacent to the function conductor.

9. The implantable medical device according to claim 1, wherein the double line is coiled.

10. The implantable medical device according to claim 1, wherein the function conductor is helically coiled in the one or more places of the medical device configured as the double line.

11. The implantable medical device according to claim 1, wherein the double line section forms a loop which is aligned parallel to the function conductor, or for a coiled electrode line, is wound into gaps of the coiled electrode line.

12. The implantable medical device according to claim 1, wherein the function conductor is surrounded by insulation that forms the dielectric, and the additional conductor is implemented with metal plating on the dielectric.

13. The implantable medical device according to claim 1, wherein the additional conductor comprises an external conductor comprising a flexible conductive polymer or liquid crystal polymer or LCP.

14. The implantable medical device according to claim 1, wherein the double line has a wave impedance of less than 120 ohms.

* * * * *